United States Patent [19]

Russell

[11] 4,030,199
[45] June 21, 1977

[54] HANDLE FOR DISPOSABLE APPLIANCE
[75] Inventor: John R. Russell, San Diego, Calif.
[73] Assignee: E-Z Floss, Palm Springs, Calif.
[22] Filed: May 12, 1975
[21] Appl. No.: 576,621
[52] U.S. Cl. .................................. 32/40 R; 15/106; 15/206
[51] Int. Cl.² ........................................ A61C 17/00
[58] Field of Search ............. 32/40 R; 30/340, 329; 15/143, 167, 106, 156, 164, 172, 206, 176; 279/23, 1 SG, 41, 43, 46; 128/267, 269, 354; 403/215, 206; 294/57

[56] References Cited
UNITED STATES PATENTS

| | | | |
|---|---|---|---|
| 1,390,924 | 9/1921 | Phillips | 279/41 X |
| 1,918,306 | 7/1933 | Williams | 403/215 |
| 3,136,040 | 6/1964 | Bauer et al. | 128/354 |
| 3,559,226 | 2/1971 | Burns | 15/206 |

FOREIGN PATENTS OR APPLICATIONS 7,975    1915    United Kingdom ................ 15/164

Primary Examiner—Robert Peshock
Attorney, Agent, or Firm—Warren, Chickering & Grunewald

[57] ABSTRACT

There is disclosed a handle for a disposable appliance that is particularly useful as a dental instrument for holding a disposable swab or brush that is mounted on a bendable stem, which device includes a handle that is of a size and shape to be manipulated with the fingers and having on at least one end a holding means for the stem. The holding means includes at least one groove of a size to receive the stem snugly and a slot located between the groove and the handle with the thickness of the slot being slightly greater than the diameter of the stem. A removable sleeve that is formed with internal contours to provide a friction fit with the holding means cooperates with the holding means, when installed thereon, to form a channel including at least one groove, the channel closely embracing the stem and holding it against slipping axially.

5 Claims, 6 Drawing Figures

HANDLE FOR DISPOSABLE APPLIANCE

BACKGROUND OF THE INVENTION

In many forms of work, particularly in dental work, it is frequently necessary to contact remote surfaces such as those between the teeth, beneath the gums, and in the interior of cavities. Frequently, contact with a soft absorbent material is required to clean the surface or to apply liquid. This has been done in the past by wrapping cotton around the end of a small stick or by grasping a cotton ball between the points of tweezers. Swabs made by such previous techniques are large, blunt, and so fixed in shape that they cannot reach remote places or be of general utility. Because of their absorbent nature and because they are too difficult to clean, swabs must be disposable; and, accordingly, they must be inexpensive.

Disposable swabs are commercially available. These are generally in the form of small absorbent tufts of cotton, nylon, or other soft material on a twisted metal stem that is made of metal that is stiff but readily bendable. Brushes and other useful appliances are also available on such metal stems. These swabs, brushes, and other appliances, to be useful, must be capable of being quickly mounted and dismounted from a handle; and the handle must be inexpensive so that it may be disposed of rather than sterilized and must be made of a material that may be maintained clean and sterile before use.

THE INVENTION

This invention is a device for holding stem-mounted, disposable appliances such as swabs or brushes for use, for example, in dental work. The device includes a handle of a size and shape to be manipulated by the fingers. Preferably the handle is about the size of a pencil. At one or both ends of the handle a means is provided for holding a stem-mounted appliance. The holding means works in cooperation with a separate sleeve or cap which has internal contours such that it fits tightly and holds by friction to the holding means when the sleeve is placed surrounding the holding means and in contact with it. The sleeve or cap has an open end through which the stem-mounted appliance protrudes. Preferably the holding means is made as an integral part of the handle with the handle and holding means being of a single piece of material such as plastic, while the sleeve is a separate piece.

The holding means includes one or more grooves which are sized to embrace snugly the stem of the stem-mounted appliance. When the sleeve engages the holding means in a friction fit, the groove or grooves become a channel closely surrounding the stem and preventing it from moving axially.

Between the handle and the groove or grooves, the holding means is provided with a slot the thickness of which is slightly greater than the diameter of the stem of the stem-mounted appliance. The groove opens into this slot. The function of the slot is to provide a means for preventing rotation of the stem-mounted appliance along its long axis as will be described hereinafter.

In one embodiment of the invention, the channel that embraces the stem may be formed between an open groove in the holding means and an interior surface of the sleeve. In a preferred form of this embodiment, the holding means is in the form of a long conical element having a slot adjacent to the handle and terminating in a shallow groove that runs to the tip of the cone. The groove is dimensioned to embrace snugly the stem of a stem-mounted appliance so that when a stem-mounted appliance is placed in the groove and the sleeve is installed with a friction fit, the interior surface of the sleeve and the groove cooperate to form an enclosed channel that snugly holds the stem, and the appliance protrudes from the end of the sleeve. The bottom portion of the stem will extend into the slot; and if this bottom portion of the stem is bent, preferably with a small, L-shaped bend at the bottom, it will form a key within the slot to prevent rotation of the stem around its long axis.

In another preferred embodiment, the holding element may comprise a conical extension from the handle that is split to form two separate, half-conical elements. Each element is formed with a groove at the outer end thereof, toward the tip of the cone, and the two elements are made of stiff but slightly flexible material. The two grooves are positioned so that when they are forced together, a channel approximately the diameter of the stem is formed. In this embodiment, the stem of a stem-mounted appliance is placed between the two grooves, and when the sleeve is installed with a friction fit, it forces the two grooves together to form a channel surrounding the stem. Again, the bottom portion of the stem protrudes into the slot between the channel and the handle and may be bent to key with the slot to avoid rotation of the stem about its long axis.

DETAILED DESCRIPTION OF THE INVENTION

This invention may be best described with reference to the accompanying drawings which illustrate preferred embodiments of the invention.

Figure 1:
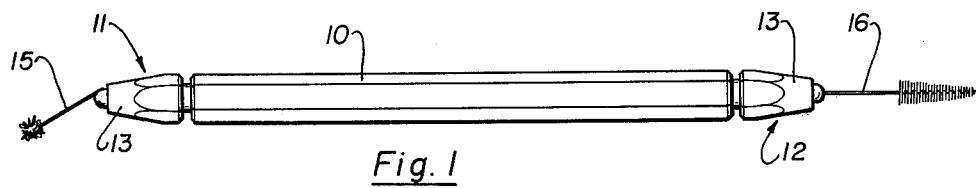
FIG. 1 illustrates an overall view of a device embodying this invention.

As can best be seen in FIG. 1, the device of this invention is the shape of a pencil and preferably the size of a pencil in that it is to be hand-held and manipulated by the fingers much in the manner of a pencil. The device has a handle portion 10 and is provided at both ends of the handle portion with a holding means such as holding means 11 and holding means 12. Each end is also surrounded with a sleeve 13, and the device is illustrated with a stem-mounted swab 15 installated in holding unit 11 and a stem-mounted brush 16 mounted in holding means 12.

FIGS. 2, 3, 5 and 6 illustrate the handle and the holding means without the sleeves 13 installed. First, describing holding means 11, a conical portion extends from the handle 10 to a rounded tip. The conical portion includes a slot 17 that extends from a point adjacent the handle 10 to the beginning of a groove 18. The groove 18 extends to the tip of the conical holding means 11. In this embodiment, the handle may be provided with a hole 20 that is simply a convenient means for bending the bottoms of the stems to appropriate angles.

Figure 3:
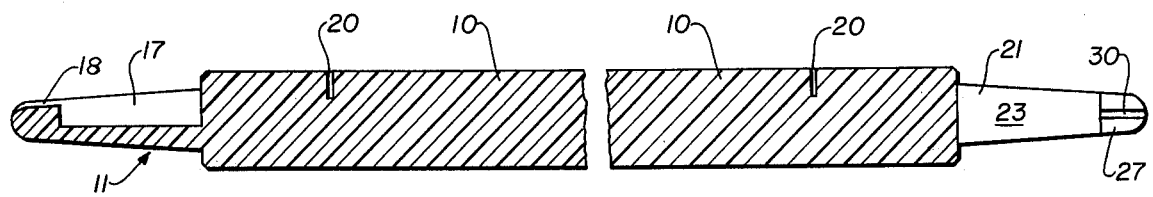
FIG. 3 is a sectional view of the device of FIG. 2 taken along the line 3—3.
Figure 2:
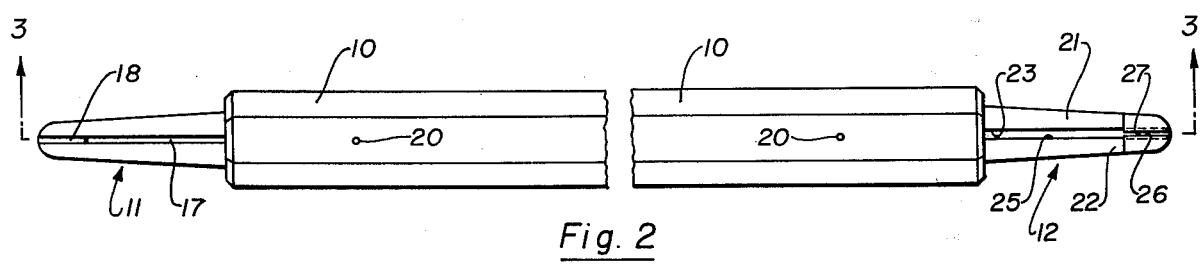
FIG. 2 is a partial elevation view of a device embodying this invention having holding means on both sides of a handle.
Figure 6:
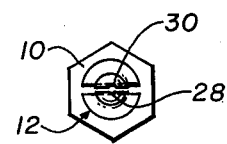
FIG. 6 is a right side view of the device illustrated in FIG. 2.

The holding means 12 is constructed with two separate but cooperating extensions 21 and 22. The extensions 21 and 22 are symmetrical and include recessed surfaces 23 and 25 adjacent the handle 10, and surfaces 26 and 27 adjacent the tip of the half-cone shapes. Surfaces 26 and 27 are provided with grooves 28 and 30, as best seen in FIGS. 3 and 6. When surfaces 26 and 27 are forced into contact, the juxtaposition of grooves 28 and 30 creates a closed channel, while the juxtaposition of recessed surfaces 23 and 25 creates a slot.

Figure 4:
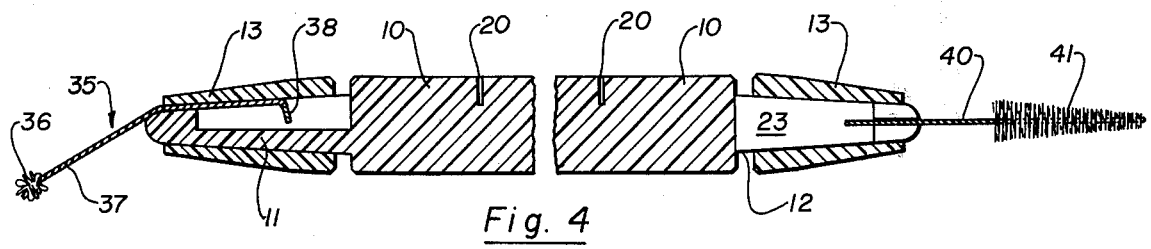
FIG. 4 is a sectional view of the device of FIG. 3 illustrating the device with sleeves in place and stem-mounted appliances installed.
Figure 5:
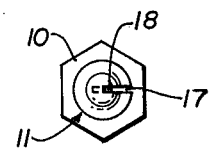
FIG. 5 is a left side view of the device illustrated in FIG. 2.

FIG. 4 illustrates the device of this invention completely assembled, having sleeves and stem-mounted appliances in place. It may be seen from FIG. 4 that in the holding element 11, a closed channel is formed between the groove 18 and the interior surface of sleeve 13. The stem-mounted appliance 35 has a soft swab end 36 and a stiff but bendable stem 37 which is usually made of twisted wire. Appliance 35 will not be described in detail in that it forms no part of this invention. Preferably the bottom tip of stem 37 is inserted into hole 20, and a sharp right angle ben is made in the stem 37. The stem 37 is then placed in the groove 18 with bent portion 38 in the slot 17, and the sleeve 13 is slid over the end of the swab and firmly pressed onto the holding element 11 unit a friction fit is accomplished. In the position illustrated in FIG. 4, the stem 37 is held tightly so that it cannot be pulled out of or pushed into the groove 18. The bent portion 38 is in contact with at least one side of the slot 17 thereby preventing axial rotation of the stem 37.

Operation of the holding means 12 may be accomplished by sliding the stem 40 of the stem-mounted brush 41 between the elements 21 and 22 and within the grooves 28 and 30, after which sleeve 13 is installed with a tight friction fit which causes elements 21 and 22 to move toward each other, thereby firmly grasping the stem 40 within the grooves 28 and 30 which are justaposed to form a channel. FIG. 4 illustrates the stem 40 without a right angle bend on the end thereof, and when strong resistance to rotation about its long axis is not required, the stem 40 may be installed in this manner. It is evident that a right angle bend in the bottom portion of the stem 40 will key the stem 40 against one or both of surfaces 23 and 25 so that the possibility of rotation about the long axis will be eliminated.

Although the device of this invention has been described with reference to being employed as a dental instrument, it is obvious that it will have more general utility. Stem-mounted appliances of this nature are useful in many activities and may be used by physicians, naturalists, repairmen, and the like, in addition to dentists.

WHAT IS CLAIMED IS:

1. A device for holding a removable, stem-mounted appliance comprising:
   a. an elongated handle shaped to be grasped by the fingers,
   b. a holding means protruding from an end of said handle, said holding means including at least one groove adapted to embrace said stem and to hold it against axial movement, and a slot between said groove and said handle, said slot opening into said groove and being slightly larger in width than in the diameter of said stem and being adapted to receive the bent end of said stem, and
   c. a removable sleeve having internal contours to form a friction fit with said holding element to surround said holding element, and, when in place on said holding element, cooperating with said holding element to form a channel including said groove, and an open end through said appliance may protrude.

2. The device of claim 1 wherein said holding means includes two bendable elements, each bendable element including a groove, and said channel is formed by cooperation between said grooves when said grooves are brought into juxtaposition by said sleeve being secured in a friction fit on said holding means.

3. The device of claim 1 wherein said channel is formed between a groove in said holding means and the interior surface of said sleeve.

4. The device of claim 1 wherein said handle and said holding element are constructed of a single piece of plastic.

5. The device of claim 1 wherein said handle has a holding element on both sides thereof.

* * * * *

UNITED STATES PATENT OFFICE
CERTIFICATE OF CORRECTION

PATENT NO. : 4,030,199
DATED : June 21, 1977
INVENTOR(S) : John R. Russell

It is certified that error appears in the above—identified patent and that said Letters Patent are hereby corrected as shown below:

In column 1, line 37, after "size" insert --and shape--.

In column 2, line 57, change "installated" to --installed--.

In column 3, line 27, change "unit" to --until--.

In column 3, line 30, after "bent" insert --bottom--.

In column 4, line 21, delete "in", second occurrence.

In column 4, line 29, after "through" add --which--.

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*